(12) United States Patent
Agdeppa et al.

(10) Patent No.: US 10,910,102 B2
(45) Date of Patent: Feb. 2, 2021

(54) IN-BED PATIENT IDENTITY VERIFICATION AND DATA COLLECTION

(71) Applicant: Hill-Rom Services, Inc., Batesville, IN (US)

(72) Inventors: Eric D. Agdeppa, Cincinnati, OH (US); Michael S. Hood, Batesville, IN (US); Laetitia Gazagnes, Montpellier (FR); Charles A. Lachenbruch, Batesville, IN (US); Michelle E. McCleerey, Raleigh, NC (US); William A. Morrison, Batesville, IN (US); David L. Ribble, Indianapolis, IN (US); Karanveer Singh, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 575 days.

(21) Appl. No.: 15/149,408

(22) Filed: May 9, 2016

(65) Prior Publication Data

US 2016/0338891 A1 Nov. 24, 2016

Related U.S. Application Data

(60) Provisional application No. 62/165,430, filed on May 22, 2015.

(51) Int. Cl.
*A61G 7/00* (2006.01)
*G16H 40/20* (2018.01)
(Continued)

(52) U.S. Cl.
CPC ......... *G16H 40/20* (2018.01); *A61B 5/02444* (2013.01); *A61B 5/113* (2013.01);
(Continued)

(58) Field of Classification Search
CPC ....... G06F 19/322; G06F 19/327; A61G 7/05; A61G 7/015
(Continued)

(56) References Cited

U.S. PATENT DOCUMENTS 7,154,397 B2 12/2006 Zerhusen et al.
7,296,312 B2 11/2007 Menkedick et al.
(Continued)

FOREIGN PATENT DOCUMENTS

EP 2641577 A2 9/2013
EP 2779002 A1 9/2014
(Continued)

OTHER PUBLICATIONS

Extended European Search Report, European Application No. 16170414.3, completed Oct. 11, 2016 (7 pages).
(Continued)

*Primary Examiner* — Trang T Nguyen
(74) *Attorney, Agent, or Firm* — Barnes & Thornburg LLP (57) ABSTRACT

A patient support system includes a patient support apparatus operable to collect biometric and/or physiological data of a patient located on the patient support apparatus, using one or more sensors that are coupled to the patient or coupled to a component of the patient support apparatus. The system can use the biometric and/or physiological data to verify the identity of a patient that is associated with the patient support apparatus or a patient room. Based on the patient verification, the system can update patient electronic medical records to include the biometric and/or physiological data, and/or perform other tasks.

24 Claims, 7 Drawing Sheets

(51) Int. Cl.
| | |
|---|---|
| *A61G 7/015* | (2006.01) |
| *G16H 10/60* | (2018.01) |
| *A61B 5/00* | (2006.01) |
| *A61B 5/1172* | (2016.01) |
| *A61B 5/024* | (2006.01) |
| *A61G 7/05* | (2006.01) |
| *A61B 5/113* | (2006.01) |
| *A61G 7/057* | (2006.01) |
| *A61B 5/11* | (2006.01) |
| *A61B 5/0402* | (2006.01) |
| *A61B 5/08* | (2006.01) |

(52) U.S. Cl.
CPC .......... *A61B 5/1172* (2013.01); *A61B 5/6891* (2013.01); *A61G 7/015* (2013.01); *A61G 7/0524* (2016.11); *G16H 10/60* (2018.01); *A61B 5/0402* (2013.01); *A61B 5/0816* (2013.01); *A61B 5/1113* (2013.01); *A61G 7/057* (2013.01); *A61G 2203/20* (2013.01); *A61G 2203/44* (2013.01); *A61G 2205/10* (2013.01); *A61G 2205/60* (2013.01)

(58) Field of Classification Search
USPC .......................................................... 705/3
See application file for complete search history.

(56) References Cited

U.S. PATENT DOCUMENTS

| | | | |
|---|---|---|---|
| 7,319,386 B2 | 1/2008 | Collins, Jr. et al. | |
| 7,515,059 B2 | 4/2009 | Price et al. | |
| 7,734,476 B2 | 6/2010 | Wildman et al. | |
| 8,266,742 B2 | 9/2012 | Andrienko | |
| 8,525,679 B2 | 9/2013 | Riley et al. | |
| 8,752,220 B2 | 6/2014 | Soderberg et al. | |
| 2006/0117188 A1* | 6/2006 | Fiske | G06F 21/32 |
| | | | 713/186 |
| 2008/0120784 A1 | 5/2008 | Warner | |
| 2009/0189769 A1* | 7/2009 | Schaffler | G06K 7/0008 |
| | | | 340/572.7 |
| 2010/0022850 A1* | 1/2010 | Mc Kenna | A61B 5/00 |
| | | | 600/301 |
| 2010/0114233 A1* | 5/2010 | Von Arx | A61N 1/08 |
| | | | 607/32 |
| 2012/0001751 A1* | 1/2012 | Baker | H04W 76/10 |
| | | | 340/539.12 |
| 2012/0089419 A1 | 4/2012 | Huster et al. | |
| 2012/0310670 A1 | 12/2012 | Pruitt | |
| 2012/0316892 A1 | 12/2012 | Huster et al. | |
| 2013/0041235 A1* | 2/2013 | Rogers | A61B 5/6867 |
| | | | 600/306 |
| 2013/0253291 A1* | 9/2013 | Dixon | A47C 21/00 |
| | | | 600/323 |
| 2013/0253950 A1 | 9/2013 | Vanderpohl, III et al. | |
| 2014/0232551 A1* | 8/2014 | Huster | H04B 5/0012 |
| | | | 340/870.3 |
| 2014/0236629 A1* | 8/2014 | Kim | G06Q 50/24 |
| | | | 705/3 |
| 2014/0266643 A1 | 9/2014 | Receveur et al. | |
| 2015/0018660 A1* | 1/2015 | Thomson | A61B 5/0404 |
| | | | 600/393 |
| 2015/0081335 A1 | 3/2015 | Dixon et al. | |
| 2015/0292856 A1* | 10/2015 | Ganton | A61B 5/6833 |
| | | | 324/671 |
| 2016/0022218 A1* | 1/2016 | Hayes | A61G 7/005 |
| | | | 600/301 |

FOREIGN PATENT DOCUMENTS

| | | |
|---|---|---|
| WO | WO 2011/120088 A1 | 10/2011 |
| WO | 2014/151577 A1 | 9/2014 |

OTHER PUBLICATIONS

Shen, T.W., Tompkins, W.J. and Hu, Y.H., One-lead ECG for Identity Verification, www.citeulike.org [*Engineering in Medicine and Biology, 2002, 24th Annual Conference and the Annual Fall Meeting of the Biomedical Engineering Society*] EMBS/BMES Conference, 2002, *Proceedings of the Second Joint*, vol. 1 (2002), pp. 62-63 vol. 1-62-63 vol. 1, doi: 10.1109/IEMBS.2002.1134388.
Sriram, Janani; Shin, Minho; Choudhury, Tanzeem; and Kotz, David, Activity-aware ECG-based Patient Authentication for Remote Health Monitoring, IMCI-MLMI '09, Nov. 2-4, 2009, Cambridge, MA, USA, pp. 297-304.
Examination Report for European Patent Application No. 16170414.3 dated Oct. 14, 2020; 5 pages.

* cited by examiner

IN-BED PATIENT IDENTITY VERIFICATION AND DATA COLLECTION

The present application claims the benefit, under 35 U.S.C. § 119(e), of U.S. Provisional Patent Application No. 62/165,430 which was filed May 22, 2015 and which is hereby incorporated by reference herein.

BACKGROUND

Patient support apparatuses, such as hospital beds, can be equipped with communications networks that allow data sharing between various modules of the patient support apparatus and with other computer systems. An example of such a bed is the VersaCare® bed available from the Hill-Rom Company, Inc. In a hospital setting, the identification and location of a particular patient is often associated with a particular patient support apparatus or hospital room. Patient support apparatuses and rooms may have a unique identifier that identifies the particular patient support apparatus or room to other computer systems, such as a health information system.

SUMMARY

The present invention comprises one or more of the features recited in the appended claims and/or the following features which, alone or in any combination, may comprise patentable subject matter.

According to one aspect of this disclosure, a patient support apparatus system includes a patient support apparatus, a sensor configured to measure data indicative of one or more physical characteristics of a patient positioned on the support apparatus; a controller in communication with the sensor and the support apparatus. The controller is configured to: select one or more features in the data for patient identity verification; and match the selected features with one or more baseline features to verify the identity of the patient. When the selected features verify the identity of the patient, the controller associates the patient with a unique identifier of the support apparatus.

In some embodiments, the sensor includes a single-lead electrocardiogram (ECG) sensor. In some embodiments, the sensor is incorporated into the linens of the support apparatus such that it contacts the mid-back region of the patient. In some embodiments, the sensor includes a biometric sensing pad, where the biometric sensing pad is a fingerprint scanner. In some embodiments, the system further includes a bed scale, where the system is configured to measure the weight of the patient at the time a fingerprint is scanned.

In some embodiments, the controller is configured to verify the identity of the patient on the patient support apparatus by comparing the measured weight to weight stored in an electronic medical record for the identified patient. In some embodiments, the sensor includes a voice recognition sensor. In some embodiments, the controller is configured to compare a voice sensed by the sensor with stored voice samples to identify the patient. In some embodiments, the controller is configured to verify the association of the identified patient with the patient support apparatus. In some embodiments, the controller is configured to generate and transmit an alert when the association is not verified. In some embodiments, the system further includes a physiological sensor, where the controller is configured to process data collected from the physiological sensor and transmit it to the identified patient.

According to another aspect of the present disclosure a controller includes a processor and a memory having stored therein a plurality of instructions. When executed by the processor the instructions cause the controller to receive sensed data from a sensor, the sensed data indicative of one or more physical characteristics of a patient supported by the patient support apparatus; compare features in the received sensed data with stored baseline features; when the features in the received sensed data match stored baseline features, verify the identity of the patient. When the identity of the patient is verified, the instructions also cause the controller to associate the identity of the patient with medical information including at least one of a unique identifier for the patient support apparatus and/or a unique identifier for a room in which the identified patient is located; and transmit the patient identity with the associated medical information to a health information system.

In some embodiments, the instructions cause the controller to associate the identified patient with a unique identifier for the patient support apparatus and/or a room in which the identified patient is located. In some embodiments, the instructions cause the controller to verify the association of the identified patient with the patient support apparatus and/or the room. In some embodiments, the instructions cause the controller to generate and transmit an alert when the association is not verified. In some embodiments, the instructions cause the controller to process data collected from a physiological sensor and transmit it to the identified patient electronic medical record (EMR). In some embodiments, the plurality of instructions cause the controller to transmit an alert if the processed data from the physiological sensor exceeds a threshold.

According to another aspect of the present disclosure, a patient support apparatus includes a frame; a surface supported by the frame, the surface configured to support a patient in at least a horizontal position; a sensor operably coupled to the patient support apparatus and configured to measure biometric data for a patient located on the patient support apparatus; and a controller coupled to the sensor. The controller is configured to: isolate one or more features of the biometric data for patient identification; match the features of the biometric data with predetermined baseline data features to identify the patient on the patient support apparatus. The controller is configured to store the biometric data in an electronic medical file of the identified patient when features of the biometric data for the patient on the patient support apparatus match the predetermined baseline data features.

In some embodiments, the controller is configured to associate the identified patient with a unique identifier for the patient support apparatus and/or a room. In some embodiments, the controller is configured to verify the association of the identified patient with the patient support apparatus and/or a room. In some embodiments, the controller is configured to generate and transmit an alert when the association is not verified.

According to another aspect of the present disclosure, a patient identification system includes a sensor carrier including a textile material configured for contact with a patient; one or more sensors integrated into the sensor carrier, where the one or more sensors are configured to measure physiological data for the patient; and a controller configured to receive and analyze the physiological data. The controller links the physiological data with verified patient association information, and stores the physiological data in an electronic medical file of the verified patient.

In some embodiments, the sensor carrier includes clothing, sheets, and/or patches. In some embodiments, one or more sensors include at least one optical sensor. In some embodiments, at least one optical sensor includes an array of reflective elements including microprisms. In some embodiments, the controller evaluates a change in reflections of the microprisms indicative of patient movement in order to determine respiratory rate of the patient. In some embodiments, at least one optical sensor includes an emitter and a detector. In some embodiments, the emitter is a fiber optic emitter that emits light of known frequencies on the skin, and where the detector is a fiber optic detector that captures light images reflected off the skin. In some embodiments, the controller is configured to analyze the reflected images to determine heart rate of the patient.

In some embodiments, the controller is configured to analyze the reflected images for skin breakdown including pressure ulcers. In some embodiments, the at least one or more sensor includes a portion configured to adhere to the skin. In some embodiments, the one or more sensors includes at least one cognitive function sensor. In some embodiments, the portion configured to adhere to the skin includes an embedded communications circuit to produce an inductive or capacitive field. In some embodiments, the at least one or more sensors includes a portion embedded in a patient support; where the portion configured to adhere to the skin and the portion embedded in the patient support combine to complete an inductive or capacitive circuit when the portions are in close proximity to each other.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION

Patient comfort can facilitate patient recovery from a health condition. The desire to improve patient comfort has resulted in a movement to reduce the obtrusiveness of monitoring equipment and sensors. However, the reduction in obtrusiveness is generally in tension with the need to properly verify the identity of the patient from whom information is being collected. Indirect identification via wearable devices such as a barcoded band introduces potential errors and misidentifications to the system, as these items can be transferred or removed. In requiring direct measurement of biometric information from the patient, proper identification and association of patient information within the health information system can be reliably obtained.

Accurate, verified patient identification and association with a patient support apparatus can permit a health information system to track the patient's health status and maintain the patient's electronic medical record through electronic communication with the patient's hospital bed. As disclosed herein, a patient support apparatus includes a patient support system that can reliably and positively identify a patient and sense physiological data for the patient at a patient support apparatus in a minimally obtrusive way. Some embodiments of the disclosed a patient support system can associate and validate identified patients at a patient support apparatus, such as a bed, and/or a patient room, in order to facilitate the collection and storage of the patient's physiological data while the patient is using the patient support apparatus.

Figure 1:
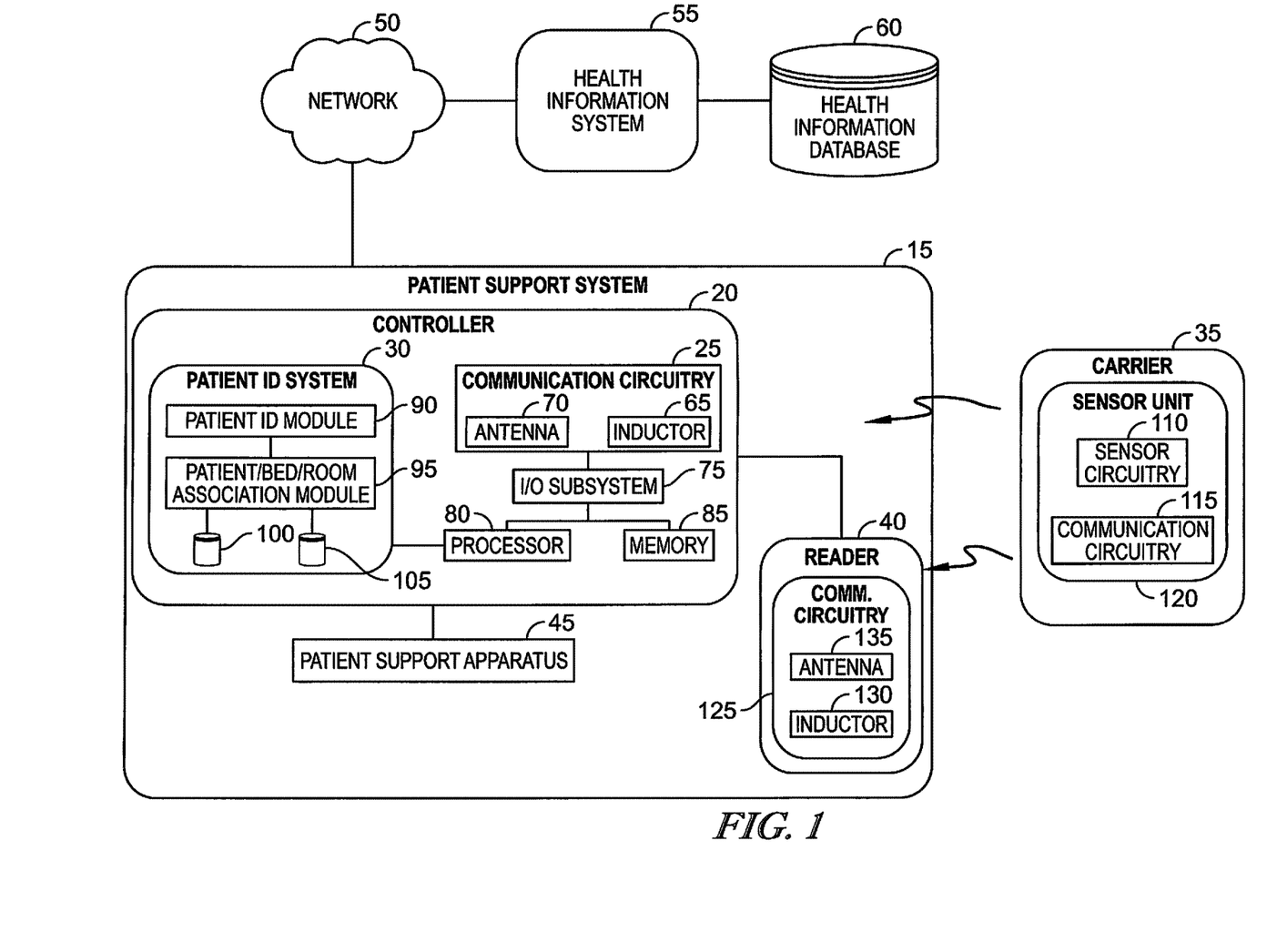
FIG. 1 is a simplified diagrammatic representation of at least one embodiment of a patient support system including a patient support apparatus, a sensor unit, and a patient identification system as disclosed herein.

Referring now to FIG. 1, an embodiment of a patient support system 15 includes a controller 20, a reader 40, and a patient support apparatus 45. A sensor carrier 35 supports a sensor unit 120. The controller 20 and/or reader 40 is configured to receive patient information from the sensor unit 120 via communication circuitry 25, 115, 125. A patient identification (ID) system 30 is embodied in the controller 20. The patient ID system 30 can identify a patient positioned on the patient support apparatus 45 based on the information obtained from the sensor unit 120. The patient ID system 30 can associate the patient whose identity has been verified with the patient support apparatus 45 and/or a patient room (not shown).

The illustrative sensor unit 120 includes sensor circuitry 110 that is operable to measure biometric and/or physiological signals of a patient. The biometric signals may be processed by controller 20 to isolate predetermined features and can be analyzed by the patient ID system 30 in order to identify the patient positioned on the patient support apparatus 45. A patient/bed/room association module 95 matches the identified patient with a unique identifier associated with the patient support apparatus 45. The patient's physiological signals may be captured by the sensor unit 120 (or another sensor unit) and processed by physiological processing module 92 embodied in the controller 20 to determine a physiological condition of the patient. The patient ID system 30 can link the collected physiological data with the verified patient identity information and sent to a network 50 to communicate with a health information system 55, and/or stored in a health information database 60, in order to update patient electronic medical records or for other reasons.

The sensor unit 120 includes the communication circuitry 115. The patient support apparatus 45 includes a controller 20 which includes the communication circuitry 25 that acts as an interface to the wireless sensor unit 120. The controller 20 also includes an I/O subsystem 75 coupled to the communication circuitry 25 as well as a processor 80 and a memory 85. The processor 80 is operable to use instructions stored in memory 85 to operate the I/O subsystem 75 which controls communication circuitry 25 as well as communication with the network 50. The controller 20 is also operable to use instructions stored in memory 85 to isolate predetermined features from data received from sensor unit 120 to communicate the predetermined features to the patient ID system 30.

The controller 20 may be programmed to operate as a universal interface capable of communicating with any of a number of different wired or wireless sensor units 120. During normal operation, controller 20 may periodically attempt to initiate communication with a wireless sensor unit such that any wireless sensor unit within the operating range of the communication circuitry 25 of the controller 20 may be detected and engaged by the controller 20.

Figure 3:
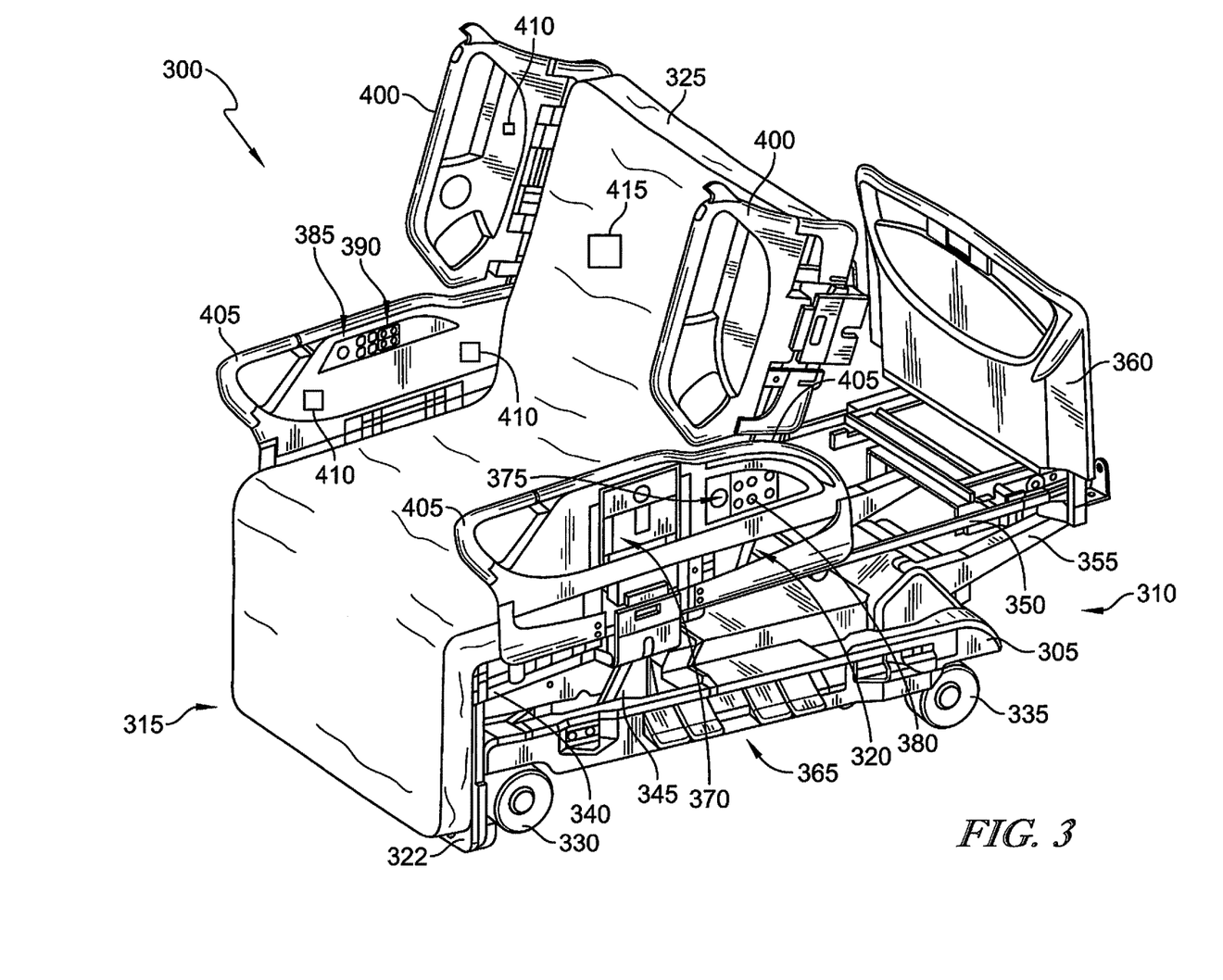
FIG. 3 is a simplified perspective view of at least one embodiment of a patient support apparatus showing one configuration of components of the patient support system of FIG. 1.

The patient support apparatus 15 may also include one or more readers 40 that are coupled to the controller 20. Each reader 40 includes communication circuitry 125 that communicates with the I/O subsystem 75 to share information with the controller 20. As shown in FIG. 3, separate readers 410 may be positioned along siderails 400, 405, in some embodiments. Additional readers may be included on head board 360 and foot board 322, or located on other parts of the patient support apparatus 45. Each of the readers 40 are optional and may be included depending on the needs of a particular application.

The illustrative communication circuitry 25 of the controller 20 includes an antenna 70 that receives the wireless signal from the sensor unit 120 and an inductor 65 that is operable to generate a magnetic field that generates a current in an inductor of the communication circuitry 115 of the wireless sensor unit 120. The communication circuitry 115 also includes a power circuit that is operable to convert the current generated in the inductor to power the communication circuitry 115 and sensor circuitry 110 of the wireless sensor unit 120. The communication circuitry 115 also includes an antenna (not shown) that transmits signals from the communication circuitry 115 to the communication circuitry 25 of the controller.

Each reader 40 includes a separate structure similar to the communication circuitry 25 of the controller 20, but are spaced apart from the controller 20 and communicate through the I/O subsystem 75. The reader 40 includes an antenna 135 and an inductor 130 that are operable to communicate with a wireless sensor unit 120. Because the wireless sensor unit 120 is a passive device, the controller 20 is operable to cause the inductor 130 of a particular reader 40 to generate a magnetic field on an intermittent basis. When the magnetic field is generated, a wireless sensor unit 120 in range of the reader 40 will receive power and begin to operate the sensor circuitry 110 and communication circuitry 115. In some embodiments, the sensor unit 120 is embodied as a radio frequency identification (RFID) tag and the reader 40 is embodied with RFID technology to receive and process signals output by the RFID tag. Other suitable wireless communication technology (e.g., infrared, Wi-Fi, etc.) may be used in other embodiments.

Sensor unit 120 can communicate sensed biometric and/or physiological data via the reader 40 or directly to the controller 20 depending on the proximity of the sensor unit 120. Sensor unit 120 is integrated into the carrier 35. The carrier 35 can be embodied as a wearable or patient-contacting material such as a hospital gown, a hospital bed mattress, a bed linen, an epidermal patch, or a tattoo-like patch.

Controller 20 is embodied as any suitable electronic device or circuitry capable of performing the functions described herein, e.g., a computing device, microcontroller, microprocessor, etc., and includes the patient ID system 30, the communication circuitry 25, an I/O subsystem 75 (e.g., a serial bus, network communications interface, etc.), a processor 80, and computer memory 85 (e.g., read-only and/or random-access memory).

The controller 20 executes instructions to isolate predetermined features from the data and communicates the features to the patient identification system 30. The patient ID system 30 includes a patient identification module 90 and a patient/bed/room association module 95, both of which are in communication with patient ID database 100 and identity verification database 105. The patient identification module 90 attempts to match the isolated features received from the processor 80 with baseline biometric features stored for admitted patients in the patient ID database 100. Identified patient data is sent to the patient/bed/room association module 95, where the identified patient data is matched with unique identifiers associated with the patient support system 15 and/or room. For example, the controller 20 may store a unique identifier for the patient support apparatus 45 to which it is mounted and/or request unique identifiers from the patient room via a pre-established hospital network. Identity verification database 105 may contain up-to-date information from an ADT (Admissions, Discharge, Transfer) system or other similar hospital information systems, including integrated hospital information systems such as Smart Connect® and SmartSync®. The patient/bed/room association module 95 may then verify that the identified patient, patient support, and/or room match the records in the identity verification database 105. Verified association data can be sent by controller 20 to the network 50 as described above. Discrepancies in association data can be sent by controller 20 to the network 50 and, for example, cause the controller 20 to send an alert to a nurse call system. In addition to or alternative to the remote verification, local verification can be provided. For instance, the patient identification can be displayed locally on a graphical user interface (GUI) at the patient support apparatus (e.g., on a graphical user interface mounted to or integrated with a siderail). The patient identification can be available wirelessly through NFC (near field communication), RFID, or a scannable barcode displayed on the GUI.

Figure 2:
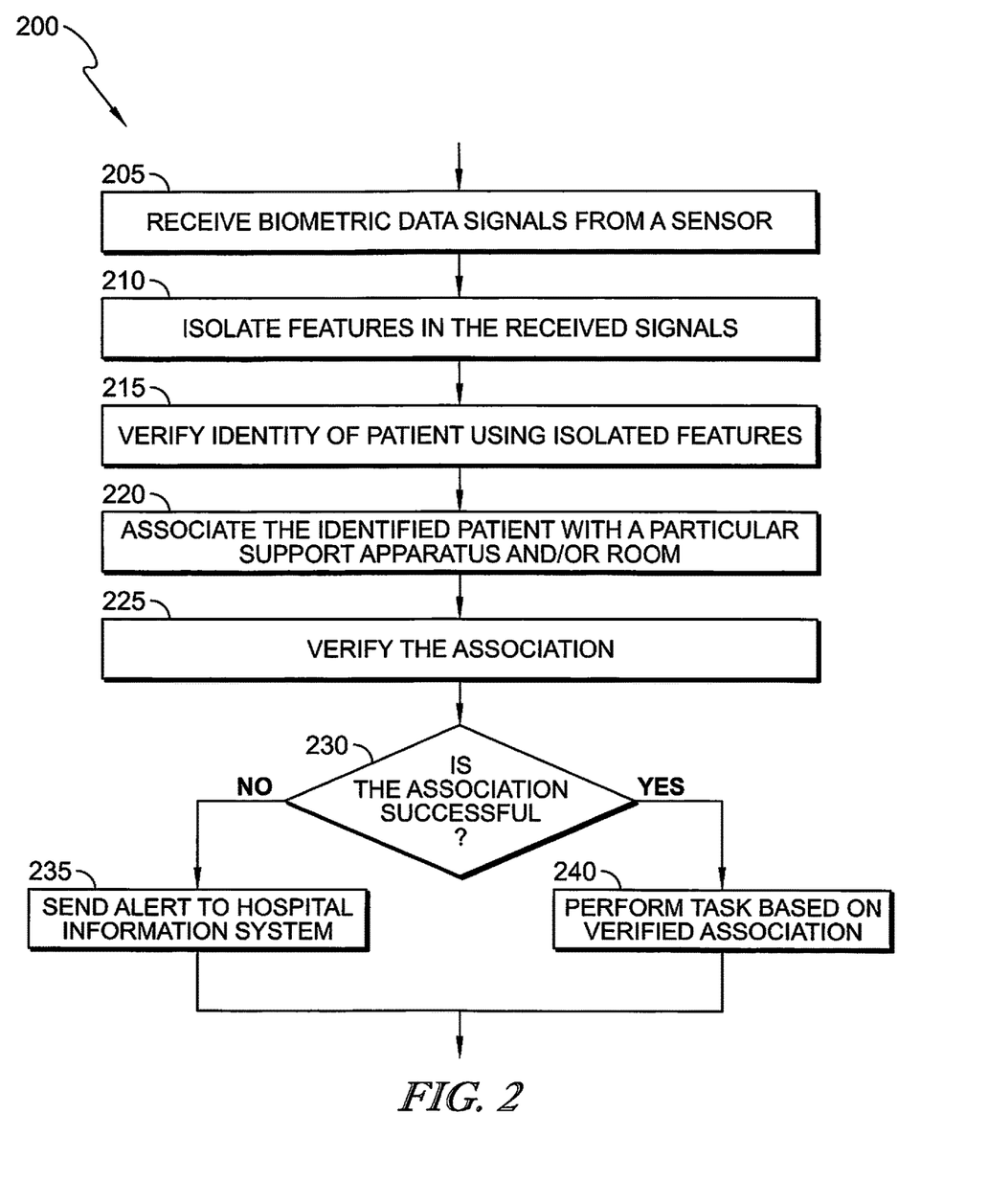
FIG. 2 is a simplified flow diagram illustrating an embodiment of an operational process of patient identity verification and association with a bed and/or room, which may be performed by the patient support system of FIG. 1.

A process 200 shown in FIG. 2 provides an overview of the various functions performed by the controller 20 in patient identification and association. The system 15 receives the biometric data signals from a patient at 205 (e.g., by a sensor unit 120). The system at 215 isolates predetermined features from the received biometric data (e.g., by one or more signal processing techniques). At 220 the system 15 compares the isolated features to baseline biometric measurements (e.g., measurements previously taken for a population of patients), and if a match is found, the system 15 verifies the identity of the patient. At 220, the system 15 associates the identified patient with a particular support apparatus that the patient is on and/or a particular room the patient is in. The identified patient and association with the support apparatus and/or room are verified by the system 15 at 225.

If the association is unsuccessful at 230, it is determined that the patient does not match the expected patient identity. This may occur, for example, if the patient is not where they are supposed to be (e.g., not in the correct patient support apparatus or room), and an alert can be sent to an appropriate hospital information system 235 such as a nurse call station and/or provided locally on a graphical user interface of the patient support apparatus 45 or another computing device (such as a caregiver's mobile computing device). The alert can be audio, and/or visual. The alert may include the patient identification and associated bed or room. The alert may also include the correct bed and or room that the patient was supposed to be in so that the patient can be relocated or the ADT records updated.

If the association is successful at 230, the system 15 may perform one or more of a variety of tasks 240 including transferring the association to a hospital network and further to the health information system along with other sensed physiological data to update electronic medical records. The association may also provide (e.g., enable/unlock) access to select peripheral devices that the particular patient is allowed to adjust on the hospital support or bed. Peripheral devices may be any of a number of subsystems of a patient support apparatus known in the art. For example if the patient support apparatus 45 is embodied as a hospital bed, a peripheral device may include any one of a scale system, siderail position monitoring system, a brake mechanism monitoring system, a bed position monitoring system, a patient position monitoring system including bed exit detection capability, or a therapy device such as a therapeutic mattress. For example, if the patient is identified with a lower body injury, he may not be permitted to adjust a lower end of the hospital bed. The association may further be used by the system to alert healthcare providers to particular physiological symptoms sensed and the current patient location.

FIG. 3 illustrates an exemplary embodiment 300 of components of the system 15, embodied in a hospital bed. The illustrative bed includes a deck 320, which has a head end 310, a midsection (or seat section) 340, and a foot end 322 spaced from the head end 310. A lift mechanism, which includes lift arms 355, is configured to raise, lower, and tilt a frame 350 relative to the base 305. A weigh scale may be coupled to the frame 350, using existing or newly developed techniques. Some examples of beds with built-in weigh scales and associated displays and user controls are disclosed in U.S. Pat. Nos. 4,934,468; 5,715,548; 6,336,235; 7,296,312; and 7,500,280. The bed includes the frame 350 coupled to the base 305 via arm 345. The base 305 is supported by a number of casters, including casters 330, 335. The casters 330, 335, each include one or more wheels that movably support the bed relative to a floor or other surface, in one or more directions. The base 305 and/or one or more of the casters 330, 335 may have an electronically or mechanically-controlled brake and/or steer lock mechanism coupled thereto. A bed controller 370 can be coupled to the lock mechanism to monitor the status of the caster brake/steer mechanism.

System 300 may include a wireless sensor unit 415 integrated into carrier 325, the carrier being a fitted sheet of a hospital mattress. Readers 410 are placed along siderails 405, 400 and can be seen on the left but also can be incorporated on the inner walls of the siderails in the right as well as head board 360. Controller 370, communicates with the readers 410 and/or sensor unit 120 as described above. The bed in this embodiment includes a plurality of patient activation controls, or buttons 385, 390 that the patient can selectively access to adjust the bed the configuration upon identification of the patient and association of the patient and bed at the controller 370. The bed also includes a plurality of caregiver controls 380, 375, 365 for making adjustments to the bed by a caregiver.

Sensor unit 415 can be any of a number of sensor units that provides sensed data that uniquely identifies a patient, or biometric data. For example, a textile integrated single-lead Electrocardiograph (ECG) electrode integrated into the bed sheet carrier 325 to measure ECG data. As shown in FIG. 3, the electrode is located in the mid-back or torso region of the linens in order to measure the ECG data. The ECG waveform can be processed at reader 410 to isolate identifying features in the QRST complex of the waveform. The isolated features constitute a "signature" that can be used to identify the patient.

Figure 4:
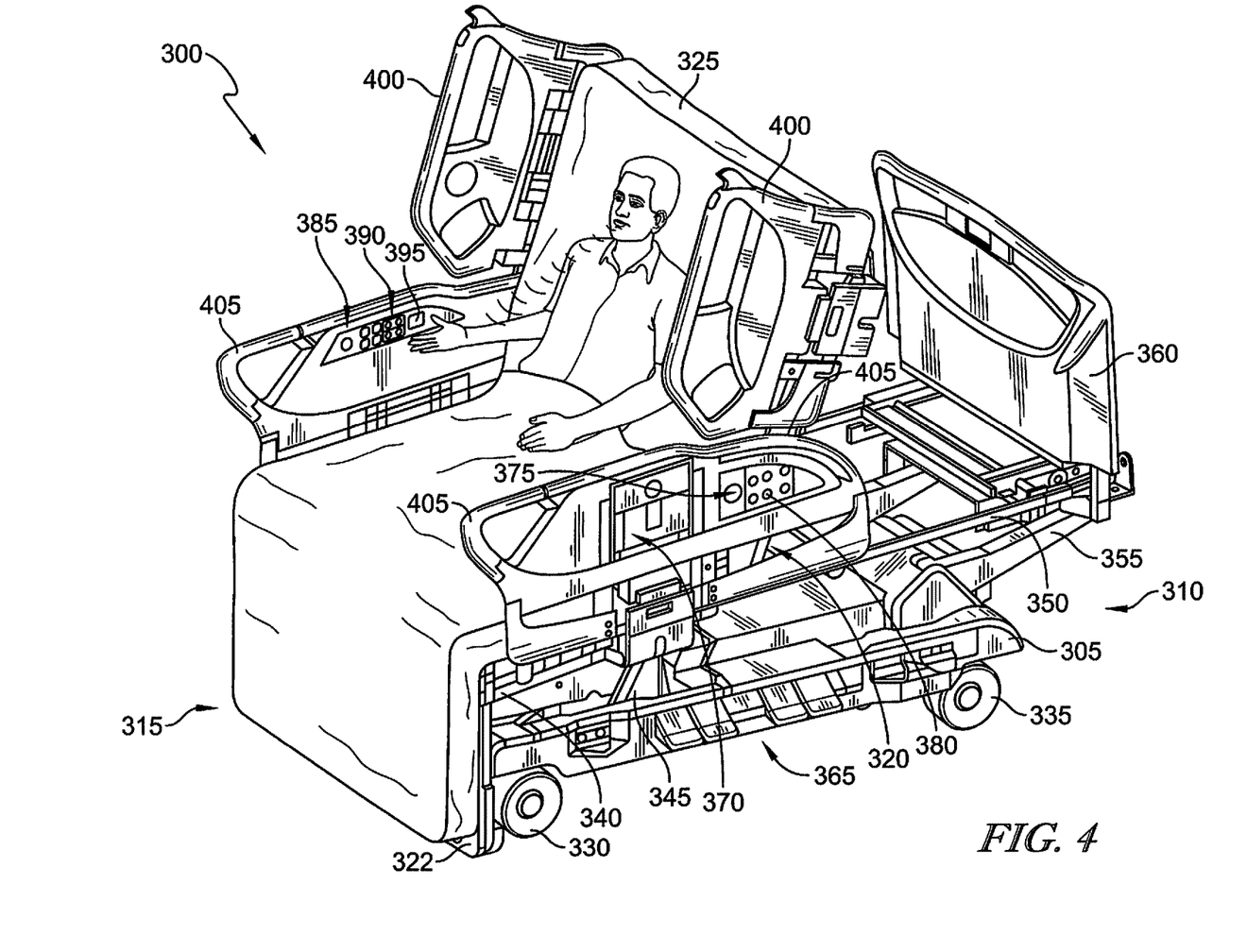
FIG. 4 is a simplified perspective view of at least one embodiment of a patient support apparatus showing another configuration of components of the patient support system of FIG. 1.

FIG. 4 illustrates another exemplary embodiment of system 300 in which a sensor carrier 395 is integrated into a lower siderail 405. Carrier 395 may combine sensor circuitry 110 along with the communication circuitry 125 of the reader shown in FIG. 1 and communicate directly with controller 370 (e.g., via a wired data connection). Alternatively, the carrier 395 and sensor circuitry 110 may be hard wired to the controller and power supply for the patient bed, negating the need for a reader. In this embodiment, sensor carrier 395 can include a voice recognition sensor (e.g., a microphone coupled with voice recognition technology) or a fingerprint scanner coupled with fingerprint recognition technology. Sensor 395 may be coupled to a lower siderail 405 for convenient access by a user's hand, or to an upper siderail 400 for convenient vocal access.

In operation of the voice recognition sensor, when a patient speaks into the sensor (e.g., by a microphone), the controller records the voice sample, recalls stored voice samples and the real-time recorded speech is compared to the stored samples via a speaker identification algorithm to identify the patient. In operation of the fingerprint scanner, when a patient presses his finger to the scanner, the controller compares the real-time fingerprint features with stored fingerprint features to identify the patient.

In this embodiment, the system 300 may further include a weigh scale coupled to the controller to indicate when a patient has entered or exited the support apparatus. The system can be configured to perform an identity check each time the bed scale indicates the patient has entered or exited the bed. Additionally, the system can be configured to create an alert using the patient weight as a secondary identifier. For example, if the patient's fingerprint or voice ID is linked to a patient weight that conflicts with the stored weight for the identified patient, a caregiver can be alerted with a notification that attention is required. This provides a safety check in case the person supplying the biometric data is not the person that is assigned to the bed by the ADT system or otherwise expected to be in the bed.

Figure 5:
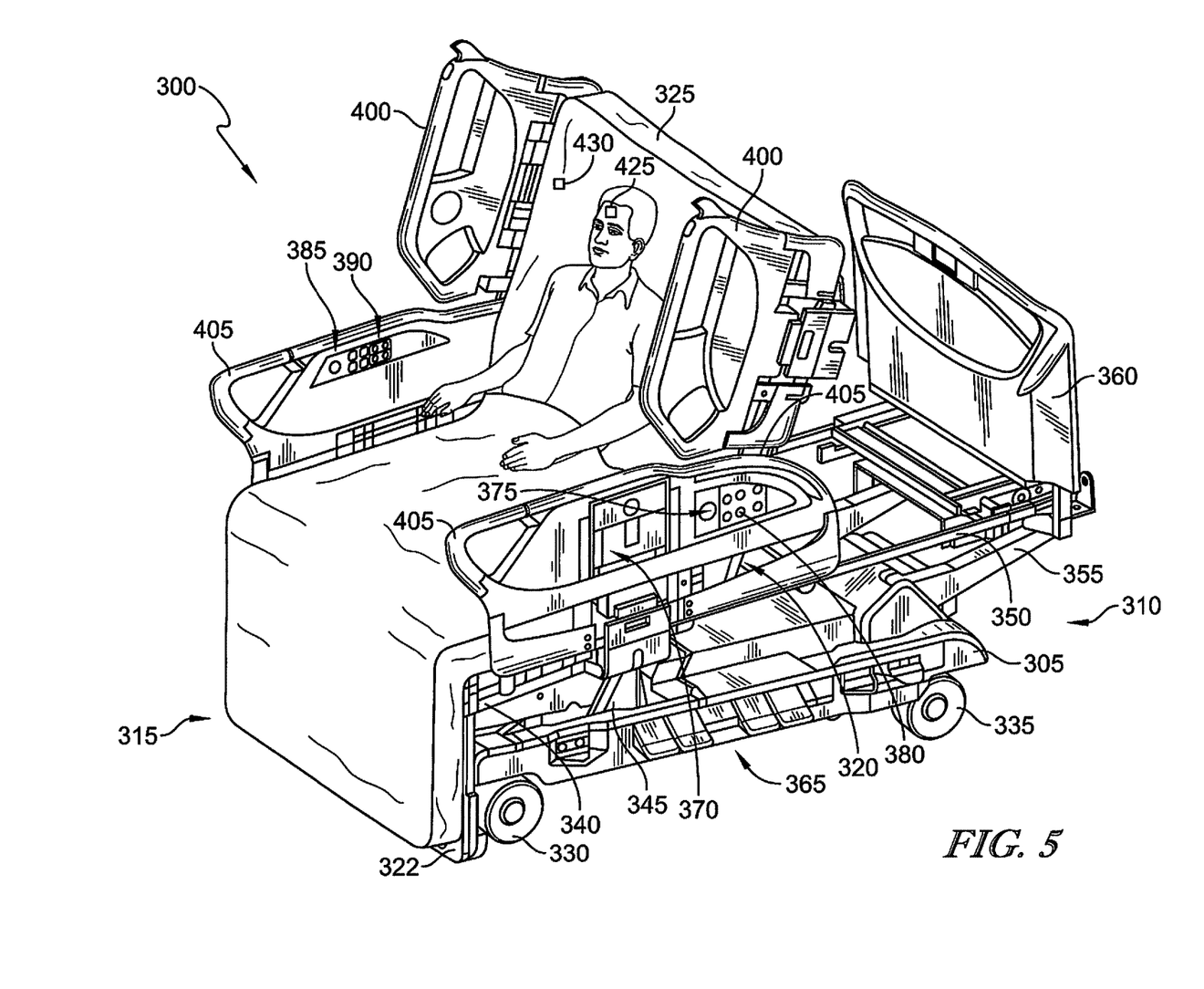
FIG. 5 is a simplified perspective view of at least one embodiment of a patient support apparatus showing another configuration of components of the patient support system of FIG. 1.
Figure 6:
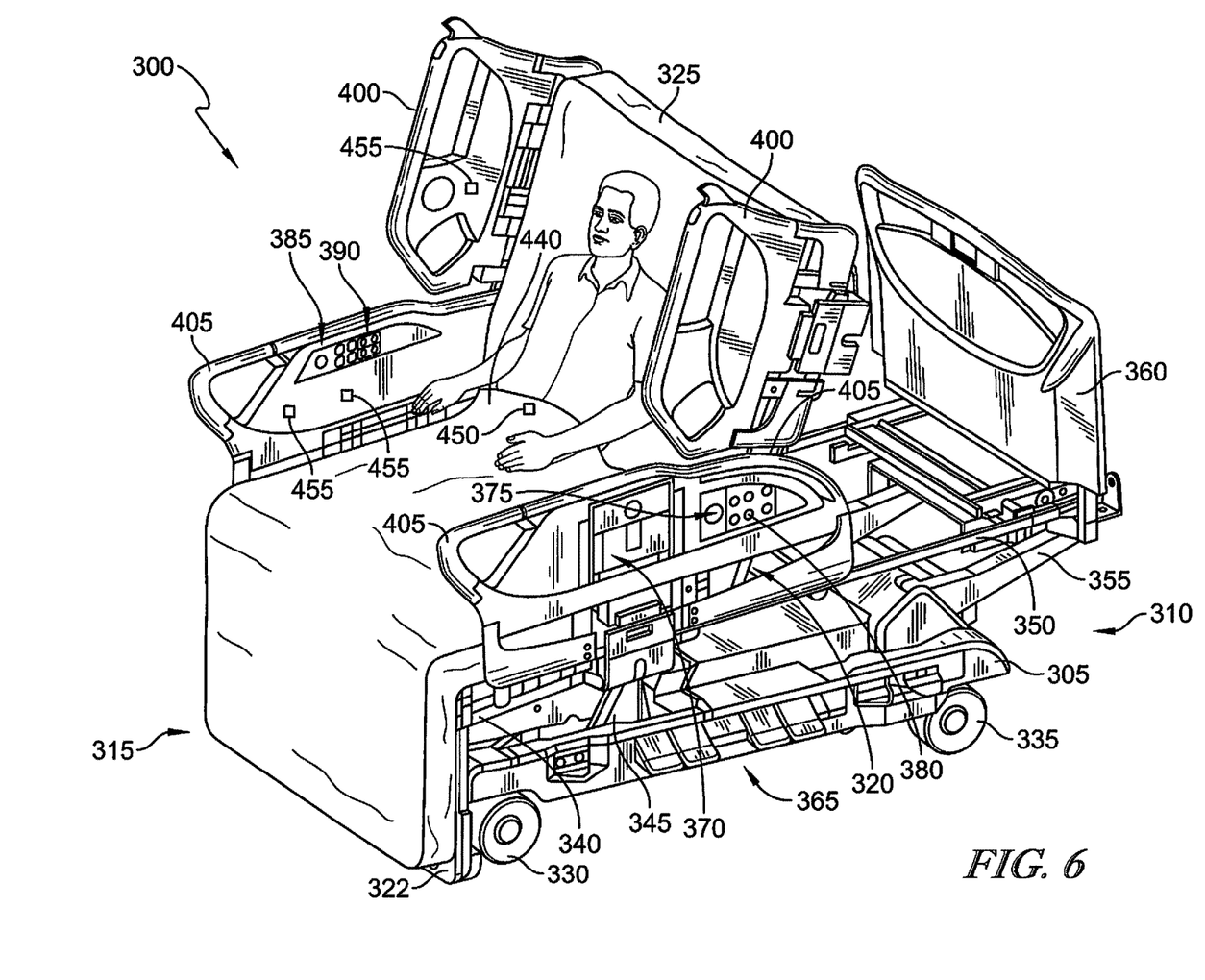
FIG. 6 is a simplified perspective view of at least one embodiment of a patient support apparatus showing another configuration of components of the patient support system of FIG. 1.
Figure 7:
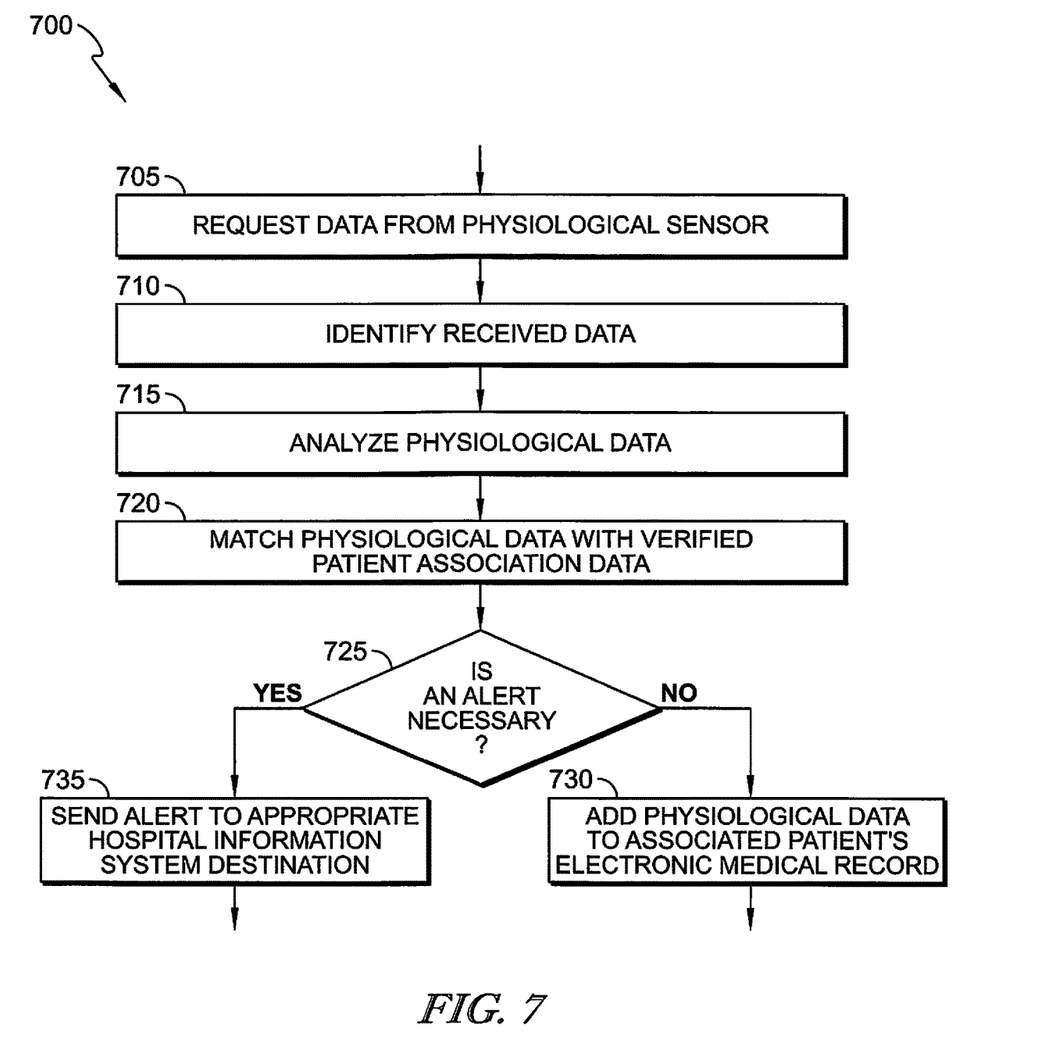
FIG. 7 is a simplified flow diagram illustrating an embodiment of an operational process of patient association with physiological sensor data, which may be performed by the patient support system of FIG. 1.

FIGS. 5-7 illustrate additional embodiments of the system 300, including various types of physiological sensors that can be used in combination with the patient support system shown in FIG. 1. Physiological sensors can be incorporated into the same sensor unit and carrier as the biometric sensors and/or additionally be placed on independent carriers to be placed at requisite sensing points on the body. Once the patient on the bed has been identified, all physiological data collected by the controller will be associated with the identified patient.

In one example of a physiological sensor illustrated in FIG. 5, the sensor unit 120 may include a wearable carrier component 425 and a non-wearable carrier component 430. The wearable carrier can be a tattoo-like-patch that resembles the skin in regard to thickness, effective elastic moduli, bending stiffness, and areal mass density. The illustrative non-wearable carrier 430 is integrated into a patient support 315. The circuits contained within the wearable carrier component 425 and the patient support 315 each comprise half of a complete circuit which can only be active when both halves are in proximity. The wearable carrier (e.g., patch) 425 contains physiologic sensing components and an embedded communications circuit capable of producing either an inductive or capacitive field that can be detected by the bed when in proximity. The bed also contains an inductive/capacitive communications circuit to provide a communications link between the two components. This eliminates the need for an electronic circuit and/or antenna in the wearable patch because the system is self-powered. In some embodiments, the two carrier components 425, 430, may act as an additional safeguard in verifying patient identity by storing unique identifiers in each component so that the circuit is only active when the particular patient with the wearable carrier component 425 is on a particular patient support 315 with the non-wearable carrier component 430.

In another example of a physiological sensor illustrated in FIG. 6, the sensor unit 450 can be integrated into a textile carrier configured for contact with the patient. For example, the sensor unit 450 can be integrated into the bed sheet 440. It is also contemplated that the sensor unit can be integrated into other textile carriers including hospital gowns and clothing, bandages, or other smart textiles worn by patients. The sensors can be powered and measurements can be taken via readers 455 placed along the bed as described above and shown in FIGS. 1 and 3.

In one example, the sensor unit 120 can be an optical sensor unit that includes a fiber optic emitter and receiver. In operation, light from the emitter may be directed at the patient's skin at known frequencies and return light may be captured by the receiver. The data can be transmitted to reader 455 which in turn transmits it to controller 370 for analysis. The controller 370 can analyze the received spectrum of returned light using multi-spectral imaging. In some embodiments the sensor unit 450 emits and detects light that the controller 370 analyzes to detect microblushes associated with each heartbeat to monitor heart rate. In some embodiments sensor unit 450 emits and detects light that controller 370 analyzes for signs of skin by scanning for frequency peaks of known peak markers of tissue breakdown or stress. Controller 370 can be configured to continuously monitor for skin breakdown to detect pressure ulcers.

In another example, the sensor unit in FIG. 6 may include may include an array of reflective elements on a surface of silk film integrated into sheet 440. Readers 455 may include infrared beam emitters to communicate with the reflective elements, for example microprisms, that can be read by machine vision in the readers 455. The read data may then be transmitted to the controller 370 which may use algorithms to correlate changes in reflections by the microprisms with patient movement associated with respiration. This allows contactless monitoring of respiration rates continuously in the dark.

A process shown in FIG. 7 provides an overview of the various actions that may be performed by the system 15 in processing data from the physiological sensors (e.g., sensor units 120) and association with the verified patient. This process may, for example, be one of the tasks that occur at 240 in FIG. 2. In operation, the system requests data from a physiological sensor on a patient at 705. At 710, the system identifies the type of received data in order to employ the correct algorithms for analysis. The physiological data is then analyzed to determine relevant physiological sensed information such as heart rate or respiratory rate at 715. At 720, the physiological data is matched to or associated with the verified patient association data, for instance by tagging it with the patient association data. At 725, the system determines if an alert is necessary. For example, the system may store a plurality of thresholds for alerts based on the analyzed physiological data. This may include a heart rate threshold, a respiratory rate threshold, a skin breakdown threshold, or any number of other thresholds relevant to sensed patient physiological conditions. If an alert is necessary, the alert is sent to an appropriate hospital information system destination, such as a nursing station at 735. The alert may be audio and/or visual and includes the verified patient association information and an indicator of what physiological condition the alert is directed to. If an alert is not necessary, the analyzed physiological data may be transferred over the network to the health information system by the controller in real time, or may be stored in memory and transferred to the network on an intermittent basis.

In still other embodiments, when the information is stored on the controller, the health information system 55 may be operable to query the controller 20 to receive the most recent information stored by controller 20 in memory 85. Controller 20 may combine and associate information from peripheral devices in the patient support apparatus 45 as well as sensor units 120 so that all of the information may be transferred to the health information system 55 as a single record. It should be understood that the network 50 may be connected to the patient support apparatus 45 through a wired data link, or the network connection may be a wireless data link.

Although certain illustrative embodiments have been described in detail above, variations and modifications exist within the scope and spirit of this disclosure as described and as defined in the following claims.

The invention claimed is:

1. A patient support system comprising:
a patient support apparatus;
at least one sensor configured to measure data indicative of one or more physical characteristics of a patient positioned on the support apparatus, the at least one sensor including a first portion configured to adhere to skin of the patient and a second portion integrated in the patient support apparatus, wherein the first portion includes an embedded communications circuit to produce an inductive or capacitive field, and the first and second portions combine to complete an inductive or capacitive circuit that operates to communicate the data from the first portion to the second portion when the first and second portions are in close proximity to each other, wherein the inductive or capacitive circuit is only active when the patient with the first portion of the at least one sensor adhered to the skin of the patient is supported on the patient support apparatus having the second portion of the at least one sensor; and
a controller in communication with the at least one sensor and the support apparatus, the controller configured to verify that unique identifiers that match are stored in the first and second portions and in response to determining that the unique identifiers that match are stored in the first and second portions, the controller proceeds to:
select one or more features in the data, other than the unique identifiers, for patient identity verification;
match the selected features with one or more baseline features to verify the identity of the patient;

associate the patient with a unique identifier of the patient support apparatus to establish an association when the selected features verify the identity of the patient, wherein the unique identifier of the patient support apparatus is different than the unique identifiers of the first and second portions of the at least one sensor; and unlock access to at least one peripheral device that the patient is permitted to adjust on the patient support apparatus in response to verifying the identity of the patient and establishing the association between the patient and the patient support apparatus.

2. The patient support system of claim 1, wherein the at least one sensor further comprises a single-lead electrocardiogram (ECG) sensor.

3. The patient support system of claim 2, wherein another sensor of the at least one sensor is incorporated into a linen of the patient support apparatus such that it contacts a mid-back region of the patient.

4. The patient support system of claim 1, wherein the at least one sensor further comprises a biometric sensor pad, the biometric sensor pad comprising a fingerprint scanner.

5. The patient support system of claim 4, further comprising a bed scale, wherein the system is configured to measure the weight of the patient at the time a fingerprint is scanned.

6. The patient support system of claim 5, wherein the controller is configured to verify the identity of the patient on the patient support apparatus by comparing the measured weight to weight stored in an electronic medical record for the identified patient.

7. The patient support system of claim 1, wherein the at least one sensor further comprises a voice recognition sensor.

8. The patient support system of claim 7, wherein the controller is configured to compare a voice sensed by the voice recognition sensor with stored voice samples to identify the patient.

9. The patient support system of claim 1, wherein the controller is configured to verify the association of the identified patient with the patient support apparatus.

10. The patent support system of claim 9, wherein the controller is configured to generate and transmit an alert when the association is not verified.

11. The patient support system of claim 1, further comprising a physiological sensor, wherein the controller is configured to process data collected from the physiological sensor and transmit it to the identified patient.

12. The patient support system of claim 11, wherein the controller is configured to transmit the physiological data to the identified patient's electronic medical record (EMR).

13. The patient support system of claim 12, wherein the controller is configured to transmit an alert if the processed data from the physiological sensor exceeds a threshold.

14. A patient support apparatus comprising:
a frame;
a surface supported by the frame, the surface configured to support a patient in at least a horizontal position;
at least one sensor operably coupled to the patient support apparatus and configured to measure biometric data for a patient located on the patient support apparatus, the at least one sensor including a first portion configured to adhere to skin of the patient and a second portion integrated in the patient support apparatus, wherein the first portion includes an embedded communications circuit to produce an inductive or capacitive field, and the first and second portions combine to complete an inductive or capacitive circuit that operates to communicate the biometric data from the first portion to the second portion when the first and second portions are in close proximity to each other, wherein the inductive or capacitive circuit is only active when the patient with the first portion of the at least one sensor adhered to the skin of the patient is supported on the patient support apparatus having the second portion of the at least one sensor; and a controller coupled to the sensor, the controller configured to verify that unique identifiers that match are stored in the first and second portions and in response to determining that the unique identifiers that match are stored in the first and second portions, the controller proceeds to:

isolate one or more features of the biometric data, other than the unique identifiers, for patient identification;

match the features of the biometric data with predetermined baseline features to identify the patient on the patient support apparatus; and when features of the biometric data for the patient on the patient support apparatus match the predetermined baseline features, store the biometric data in an electronic medical file of the identified patient; and unlock access to at least one peripheral device that the patient is permitted to adjust on the patient support apparatus in response to verifying the identity of the patient and establishing an association between the patient and the patient support apparatus.

15. The patient support apparatus of claim 14, wherein the at least one sensor further comprises a single-lead electrocardiogram (ECG) sensor.

16. The patient support apparatus of claim 15, wherein another sensor of the at least one sensor is incorporated into a linen of the patient support apparatus such that it contacts a mid-back region of the patient.

17. The patient support apparatus of claim 14, wherein the at least one sensor further comprises a biometric sensing pad, the biometric sensor pad being a fingerprint scanner.

18. The patient support apparatus of claim 17, further comprising a bed scale, wherein the system is configured to measure the weight of the patient at the time a fingerprint is scanned.

19. The patient support apparatus of claim 18, wherein the controller is configured to verify the identity of the patient on the patient support apparatus by comparing the measured weight to weight stored in an electronic medical record for the identified patient.

20. The patient support apparatus of claim 14, wherein the at least one sensor further comprises a voice recognition sensor.

21. The patient support apparatus of claim 20, wherein the controller is configured to compare a voice sensed by the voice recognition sensor with stored voice samples to identify the patient.

22. The patient support apparatus of claim 14, wherein the controller is configured to associate the identified patient with a unique identifier for the patient support apparatus and/or a room.

23. The patient support apparatus of claim 22, wherein the controller is configured to verify the association of the identified patient with the patient support apparatus and/or a room.

24. The patent support apparatus of claim 23, wherein the controller is configured to generate and transmit an alert when the association is not verified.

\* \* \* \* \*

UNITED STATES PATENT AND TRADEMARK OFFICE
CERTIFICATE OF CORRECTION

PATENT NO. : 10,910,102 B2  
APPLICATION NO. : 15/149408  
DATED : February 2, 2021  
INVENTOR(S) : Eric D. Agdeppa et al.

Page 1 of 1

It is certified that error appears in the above-identified patent and that said Letters Patent is hereby corrected as shown below:

In the Claims

In Claim 10, Column 11, Line 42, delete "patent" and insert in its place --patient--.

In Claim 24, Column 13, Line 1, delete "patent" and insert in its place --patient--.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*